US005685716A

United States Patent [19]
Linkow

[11] Patent Number: 5,685,716
[45] Date of Patent: Nov. 11, 1997

[54] APPARATUS AND METHOD FOR CLOSING A SINUS OPENING DURING A DENTAL IMPLANT OPERATION

[76] Inventor: Leonard I. Linkow, 1530 Palisade Ave., Fort Lee, N.J. 07024

[21] Appl. No.: 475,884

[22] Filed: Jun. 7, 1995

Related U.S. Application Data

[63] Continuation-in-part of Ser. No. 327,458, Oct. 21, 1994, Pat. No. 5,547,378.

[51] Int. Cl.$^6$ .................................................. A61C 8/00
[52] U.S. Cl. .................................. 433/173; 433/215
[58] Field of Search .................................. 433/173, 215

[56] References Cited

U.S. PATENT DOCUMENTS

| | | | |
|---|---|---|---|
| 3,088,242 | 5/1963 | Rockovits | 446/220 |
| 3,108,396 | 10/1963 | Dorman | 446/220 |
| 4,430,760 | 2/1984 | Smestad | 623/10 |
| 4,599,085 | 7/1986 | Reiss et al. | 433/173 X |
| 4,657,548 | 4/1987 | Nichols | 623/10 |
| 4,682,951 | 7/1987 | Linkow | 433/173 |

*Primary Examiner*—Robert P. Swiatek
*Assistant Examiner*—Yvonne R. Abbott
*Attorney, Agent, or Firm*—Darby & Darby

[57] ABSTRACT

An apparatus and method by which a sinus lift operation can be continued in the presence of a tear in the Schneiderian membrane covering the floor of the sinus cavity prior to installing a dental implant in an edentulous region. During such an operation, an incision is made through the tissue covering the dental ridge and an opening is created through the maxillary bone toward the sinus cavity for the purpose of inserting bone fragments under the Schneiderian membrane on the floor of the cavity. If the membrane is torn, a balloon is inserted into the opening through the maxillary bone and the membrane into the sinus cavity, such that the closed end of the balloon extends into the sinus cavity and its open end or lips are adjacent the opening at the surface of the dental ridge. The balloon lips are fastened to the dental ridge surrounding the opening, for example, by adhesive. Bone fragments are inserted into the balloon such that a lower portion of the sinus cavity is filled with the balloon portion that contains the fragments. The fragments continue to be inserted into the balloon until the opening leading to the dental ridge is completely filled. The ridge is closed and time is allowed to pass for the bone chips and/or fragments to fuse with each other and with the surrounding bone. This creates additional bone in the edentulous region which will accommodate a dental implant. The closed end of the balloon within the sinus cavity can have folds to permit expansion into a fan-like shape.

15 Claims, 4 Drawing Sheets

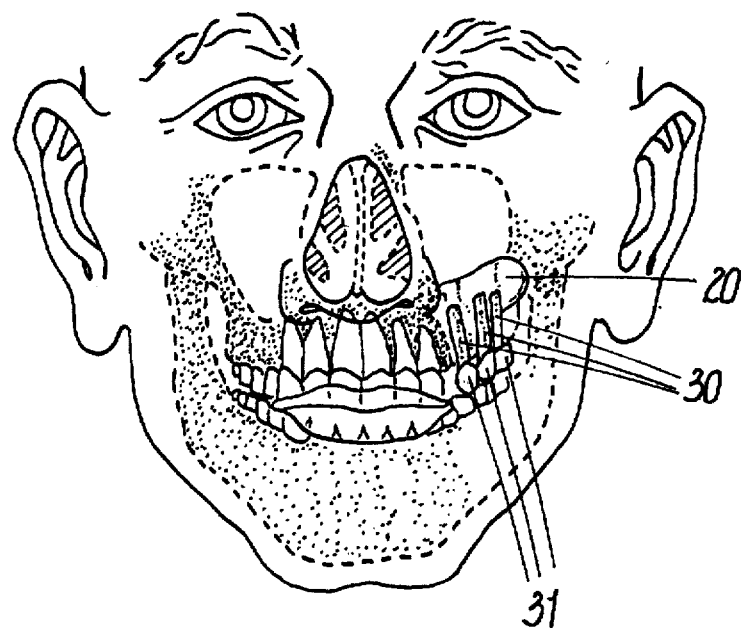
Fig. 7
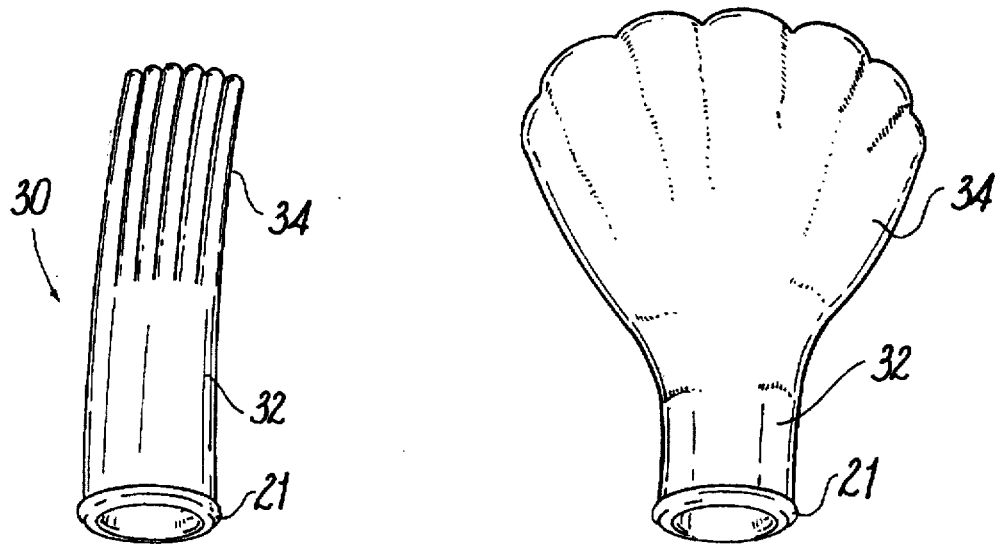
Fig. 8  Fig. 8A

APPARATUS AND METHOD FOR CLOSING A SINUS OPENING DURING A DENTAL IMPLANT OPERATION

RELATED APPLICATION

This application is a continuation-in-part application of Ser. No. 08/327,458 filed Oct. 21, 1994, now U.S. Pat. No. 5,547,378.

BACKGROUND OF THE INVENTION

This invention relates to apparatus and a method of augmenting the maxilla of a candidate for a dental implant by filling part of the patient's maxillary sinus cavity with bone and, more particularly, to a device that closes the sinus cavity when the Schneiderian membrane is torn during surgery intended to lift the membrane from the floor of the sinus cavity and add bone under the membrane.

The maxillary sinuses of a person are located on each side of the maxilla between the canine eminence and the tuberosity. The lowest point of the sinus floor usually lies superior to the first molar and the second premolar. However, maxillary sinus shapes vary greatly from one side of a person's face to the other, and from individual to individual.

As a person ages, the maxillary sinuses grow at the expense of the bone. Also, disease may cause resorption of the bone surrounding the sinus. When bone loss occurs between the sinus floor and the dental arch, the feasibility of using maxillary dental implants is decreased.

Dental or oral implants are blades or screws with attached posts. These implants are surgically implanted in a patient's mandible or maxilla along the occlusal plane. The implantation is achieved by exposing the bone with an incision through the gum tissue and creating a groove or bore in the bone with a burr or drill. The implant blade is then wedged into the groove or bore so that the post protrudes. In the currently used technique, the incision is closed for most implants and the implant is allowed to remain buried for six months beneath the bone and soft tissue so that it integrates with the bone. The tissue is then reopened and an abutment post for supporting an artificial dental appliance is screwed on to the implant. Then the tissue is sutured about the bone and the base of the post. Finally, the post is used to mount the artificial dental appliance, such as a bridge. This procedure can be carried out in stages over several months.

A patient with an enlarged maxillary sinus has little bone in the maxillary dental arch for accommodating the insertion of an implant. Consequently, the implantation procedure may result in the penetration of the Schneiderian membrane on the sinus floor and the sinus itself. This may promote sinus infection and may result in the implant being only loosely held in the remaining bone, so that it fails to function effectively as a support for artificial teeth.

In U.S. Pat. No. 4,521,192 of the present inventor, there is disclosed a technique for lifting the Schneiderian membrane and locating bone fragments beneath it in order to thicken the bone at the sinus floor by regrowth of new bone around the inserted bone fragments. According to this disclosure, an implant is used which has a basket or cradle built into the blade portion. This basket is open toward the groove in the patient's bone and is filled with bone chips or fragments. Consequently, when the implant blade is wedged in the groove, the basket is moved to the base of the groove which, if the Schneiderian membrane is exposed, pushes the membrane upward into the maxillary sinus cavity.

The depth at which the blade of an implant is located in the patient's bone cannot be varied to any great extent with this device. Thus, with this prior device, in which the basket is fixed to the blade portion of the implant, there is little control over the degree to which the Schneiderian membrane is lifted. This limits the oral surgeon's ability to increase the thickness of bone at the floor of the sinus cavity and to make it suitable for the retention of the implant.

Another technique for augmenting the mandible of a patient with additional bone in order to support a dental implant is disclosed in U.S. Pat. No. 4,682,951 of the present inventor. According to the disclosure in that patent a bone chip container which is adjustably secured to the implant is used for installing the implant in the maxilla of a patient in which the bone of the dental arch in an edentulous span is thin because of a descending maxillary sinus. In using the device, an edentulous area of the dental arch of the maxilla is exposed. A groove is made in the bone mesial and distal to the floor of the sinus, and up to the Schneiderian membrane, which membrane lies on the floor of the maxillary sinus. In addition a larger opening is made through the bone toward the center of the groove. Then an especially designed sinus lift implant is installed in the groove.

The sinus lift implant has a container which is open at one side such that it is in the form of a cradle or basket. The basket has a size such that it can pass through the opening at the center of the groove made in the bone. Threaded apertures are located in the bottom of the basket of the blade and threaded shafts engage these apertures. The blade or base portion of the implant is narrow, at least at its ends, so that it can be wedged tightly in a portion of the groove in the bone at such a depth that the base does not extend downwardly from the maxilla beyond the existing bone of the dental arch. One or more posts project downwardly from the base and can be used to mount an artificial tooth structure from the maxilla.

During installation, the open basket is filled with bone chips, either natural or artificial. Then the basket is passed up into the large opening in the maxilla below the Schneiderian membrane. The blade portions (mesial and distal) to the basket are then tapped into place so that the implant is wedged in the groove and the basket is at least flush with the alveolar crest. Access to the ends of the threaded shafts are provided through the bottom of the apertures in the base so that the shafts can be rotated. Rotation of these shafts raises, lowers or tilts the basket to redefine the shape and thickness of the sinus floor. The basket is then moved high into the maxillary sinus, although still below the Schneiderian membrane. Its base is now well above the alveolar crest so that it is easy to suture close the tissues beneath it.

Once in position, the gum tissue is sutured closed over the base portion. During a period of several weeks or months, new bone will grow and fuse with the surrounding bone and chips. This results in a thicker bone area enclosing the implant and a reduction in the size of the sinus. After the formation of the new bone, the artificial tooth structure is mounted on the post of the implant, which post protrudes beyond the gum tissue.

The posts themselves can be made independently from the implant itself, thus allowing the implant to be completely submerged during the healing process. Presently, if only tiny tears are made in the Schneiderian membrane, it is known to patch the tear with a flat piece of non-absorbable guided tissue membranes, such as Tef Gen FD (PTFE) as well as resorbable VICRYL. However, this does not provide adequate support for stabilizing bone chips placed under the membrane until they fuse.

SUMMARY OF THE INVENTION

The present invention is directed to eliminating the need to halt a sinus lift operation when the Schneiderian membrane is torn. This is accomplished by inserting a balloon into the opening in the torn membrane and using it to create a cavity into which bone fragments are inserted for the purpose of augmenting the maxilla so it can better support a dental implant.

In an illustrative embodiment of the invention a tiny balloon, e.g. a finger type balloon, is pushed into the sinus opening and the lips of the balloon are glued to the bony walls of the crestal bone which surround the opening. When the glue dries firm, a small air pump may be inserted inside of the balloon and is used to pump it up so it more closely adapts to the shape of the inner walls of the sinus.

Bone from the iliac crest, freeze dried bone, bone from the symphysis, synthetic bone such as calcitite (non-resorbable) and osteogen (resorbable) hydroxyapatite, as well as any other acceptable bone elements are syringed into the balloon. This fills the balloon and reduces the internal air pressure. The amount of the bone elements which is syringed into the balloon is the amount which is necessary to achieve the desired morphological shape of the sinus walls. However, the bone elements do not fill up the entire sinus at any time.

The reason for inserting the air in the balloon is to give shape to the balloon and make it easier to introduce the bone elements. Helium or some other gas, such as oxygen, may be used to inflate the balloon and in some instances inflation may not be necessary at all. When in place, the balloon both protects and replaces the Schneiderian tissue. The balloon is primarily used when no evidence of a Schneiderian membrane remains due to its enucleation as well as the enucleation of all polypoidal and granulomatous tissue that may exist from a previous chronic long standing infection.

BRIEF DESCRIPTION OF THE DRAWINGS

The foregoing and other features of the present invention will be more readily apparent from the following detailed description and drawings of an illustrative embodiment of the invention in which:

FIG. 7 illustrates four root form implants installed in bone augmenting the maxilla as a result of a sinus lift operation according to the present invention;

FIG. 8 is a perspective view of another form of balloon; and

FIG. 8A is a view of the balloon of FIG. 8 when inflated.

DESCRIPTION OF AN ILLUSTRATIVE EXEMPLARY EMBODIMENT

Figure 1:
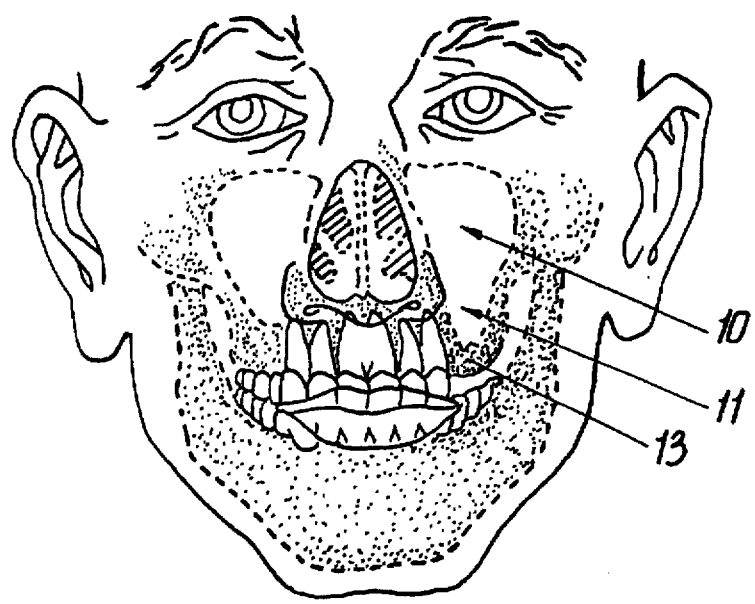
FIG. 1 is a schematic view of the face of a patient with a low maxillary sinus showing a portion transparent so that mandible and maxillary bones, the teeth and the maxillary sinus cavity are visible.

FIG. 1 illustrates an enlarged descending maxillary sinus cavity 10 of a potential dental implant patient. The descending portion 11 could be the result of disease, e.g., severe mandibular atrophy, or it could be congenital. Regardless of the cause, the effect is to produce dehiscency of the interior border so there is a very small amount of bone between the sinus cavity 10 and the alveolar ridge crest 13. Thus, if a root form or blade-type of dental implant is to be installed in an edentulous region in that vicinity, there is very little bone in which the implant can be anchored.

Figure 2:
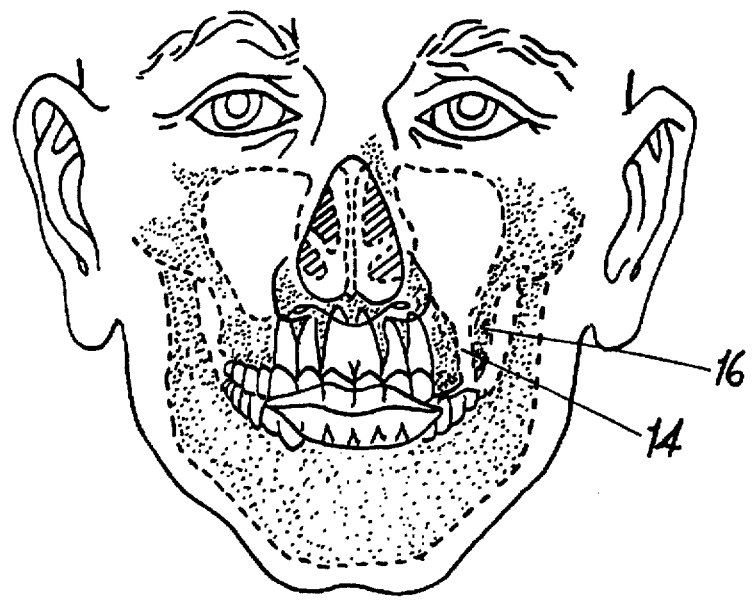
FIG. 2 is a view similar to FIG. 1, but showing the removal of maxillary bone and the tearing of the Schneiderian membrane during a sinus lift operation.

The interior of the sinus cavity 10 is covered with a membrane known as the Schneiderian membrane. During a sinus lift operation an incision is made in the tissue covering the alveolar ridge 13, either at the crest of from the buccal side. The tissue is then reflected to expose the underlying maxillary bone. Using a dental drill a channel 14 is created in the bone from the surface of the ridge 13 to the cavity 10 as shown in FIG. 2. During this process, care must be taken to avoid tearing the Schneiderian membrane 16 which covers the floor of the sinus cavity 10. The Schneiderian membrane is, however, separated from the floor of the sinus cavity and is lifted upwardly into the cavity. Various means are then used to pack bone chips into the lower area 11 underneath the Schneiderian membrane, which membrane acts to prevent bacteria from traveling from the site of the implant into the sinus cavity.

Most often, the raising of sinus is accomplished through a lateral buccal approach by making a rectangular bore in the bone and infracturing this bone to become the new sinus floor. However, because of tearing of the membrane, the procedure must often be aborted. In particular, if as shown in FIG. 2, during the course of the sinus lift operation when the channel 14 is drilled, e.g., from the buccal side of the ridge 13 into the cavity 10, the Schneiderian membrane 16 is torn, an attempt to lift the sinus floor by inserting bone chips into channel 14 would cause problems. First, there would be nothing to prevent the bone fragments from entering into the cavity 10 and rattling around freely in the cavity. Second, bacteria and other germs could enter the cavity through the channel 14 and the torn Schneiderian membrane 16.

Figure 3:
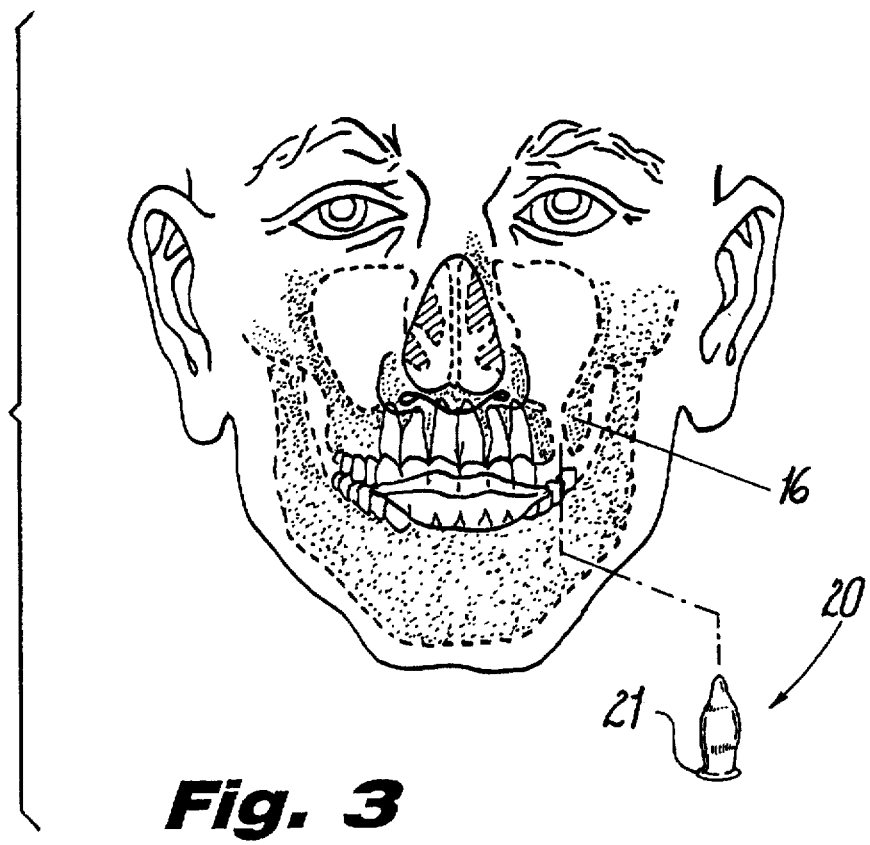
FIG. 3 is the same as FIG. 2, but illustrating a balloon useful in practicing the present invention.
Figure 4:
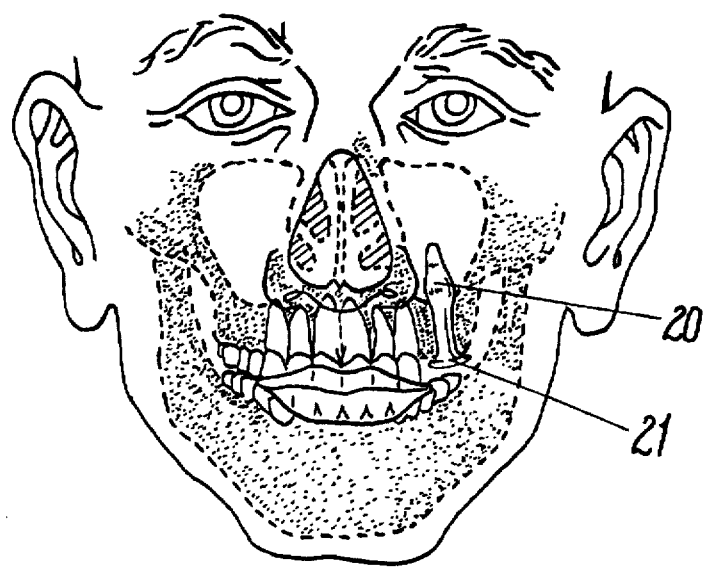
FIG. 4 shows the balloon of FIG. 3 inserted through a tear in the Schneiderian membrane and into the maxillary sinus cavity.

The present invention addresses the problem of a torn Schneiderian membrane by means of a small inflatable balloon 20 shown in FIG. 3. Suitable materials for the balloon are described below. As shown in FIG. 4, the balloon 20 is inserted in the channel 14 so that it extends into the sinus cavity 10. Prior to insertion of the balloon, the large dehiscent antral opening is cleared by using various shaped curettes to remove all granulomatous, polypoidal and diseased tissues from the bony walls concomitantly with sterile saline irrigation until only the osseous walls remain.

The lips 21 of the balloon are glued or otherwise fastened to the exposed bone of the alveolar ridge crest in the area surrounding the channel 14. A suitable adhesive is a cyano acrylate cement. At the end of the surgery, when the tissue covering ridge 13 is returned to its normal position and stitched in place, it will cover over the lips 21 of the balloon 20.

Figure 5:
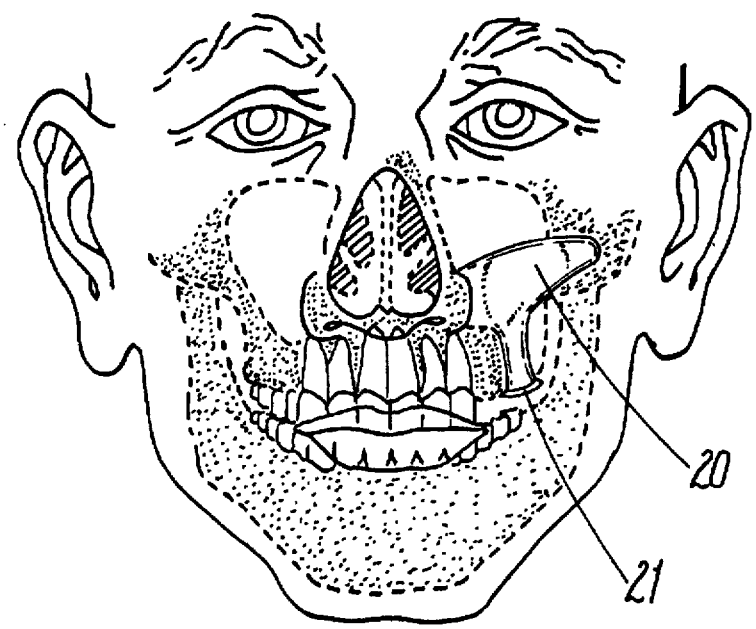
FIG. 5 illustrates the balloon in an inflated state in the sinus cavity.
Figure 6:
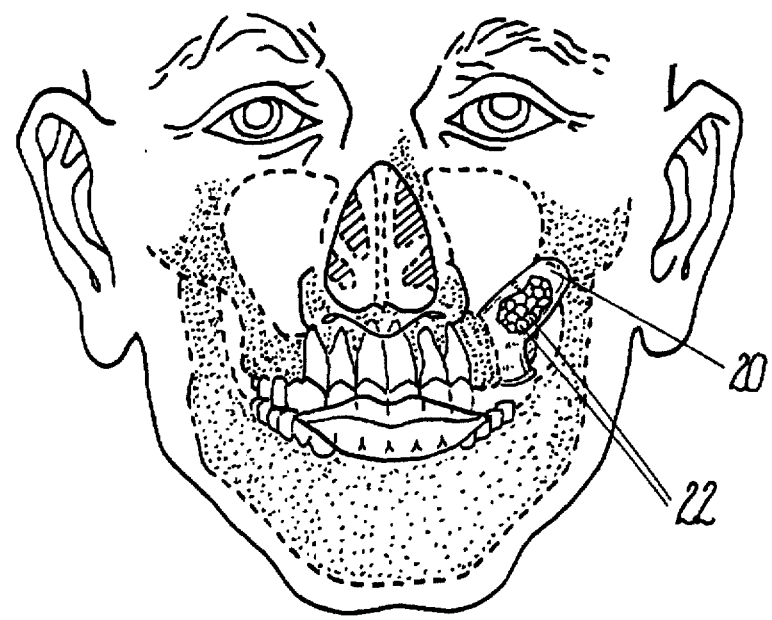
FIG. 6 is a view of the balloon with bone fragments inserted.

Prior to closing the tissue, air, helium of some other gas is injected into the balloon through the opening between its lips. Sufficient gas is pumped into the balloon by a tiny bulb pump (not shown) that fits into the balloon opening to cause inflation by a desired amount, i.e., so the balloon conforms to the inner walls of the sinus cavity as shown in FIG. 5. Catheters used for balloon angioplasty can be used in the present invention. Such a catheter allows the balloon at its end to be inserted in the channel. Further, it already has a source of gas, e.g. helium, for inflating the balloon if necessary. If the balloon is made so that it naturally stays open, the inflation step can be eliminated.

It should be noted that the dotted outline illustrating the sinus cavity 10 in FIGS. 1-7 represents only a portion of the cavity at a particular cross section. Just above the alveolar ridge crest the cavity actually extends beyond the dotted area in the mesial or distal direction, as well in a bucco-lingual direction as shown by the balloon 20 in FIG. 5.

After the balloon is put in place and inflated, if necessary, or simultaneously with inflation thereof, bone fragments 22 are inserted, such as by being syringed into the interior of the balloon. These fragments eventually act to displace air from the balloon (FIG. 6), i.e., as the fragments are pushed into the balloon, air is expelled. Enough bone should be syringed into the balloon to maintain a maximum amount of balloon inflation. This process is continued until the lower portion of the sinus cavity 11 and the channel 14 are filled with bone chips. The top portion of the balloon acts as a new raised sinus floor under which the new bone 22 is deposited. These bone fragments may be bone from the iliac crest, freeze dried bone from the symphysis, or synthetic bone, such as calcite (non-resorbable) and osteogen (resorbable) hydroxyapatite.

Once the balloon is in place and filled with bone, the underlying mucoperiosteal tissues are then sutured closed. The blood supply to the bone filled balloon will come from the periosteum as well as various blood vessels that will permeate through fenestrations or perforations formed in the balloon, either naturally during resorption of the balloon or which have been installed in the balloon, both as described below. The channel 14 at the surface of the ridge adjacent the balloon lips 21 may be closed with a cap and the tissue of the ridge sutured back into place. Over a period of time, if the balloon is made of resorbable material, the balloon will dissolve and new bone will grow under the raised sinus floor using the bone fragments as starting points. Also, as the membrane resorbs, a new Schneiderian membrane can regenerate. The end result will be an augmented maxilla suitable for implantation.

The balloon may also be formed in two parts where the upper part is non-resorbable and the lower part leading to the lips is resorbable. In such a situation, the balloon continues to act as a Schneiderian membrane even after the lower portion has dissolved, allowing new bone to grow underneath it.

When the new bone has been firmly established (e.g., in about six months to one year), as confirmed by x-rays, the tissue covering the alveolar ridge crest 13 may again be opened and this time dental implants, for example, blades or root-form implants 30, may be inserted into the new bone in such a manner that they support artificial teeth 31 in the edentulous region. This is shown in FIG. 7.

The balloon for use in the present invention may be manufactured from various types of material. These materials can be slowly resorbable and elastic, inert and acceptable biocompatably with the bone in the area. For example, the material can be similar to Gortex, except that it should be resorbable, such as polycarbonate. Another resorbable material is Hyaluronate, which is a cross-linked knitted material that resorbs in about 8–12 weeks and is available from Life Core of Minneapolis, Minn. Further the balloon can be made from esters of hyaluronic acid available from FIDIA Advanced Biopolymers of Abano Terme, Italy. The resorption of the balloon also the blood supply to be reestablished with the new bone.

Elastomeric material can be inflated so it is usable for the balloon in this respect, but it is also non-resorbable so it could prevent new bone growth. Such material can be made to work, however, by forming it with many tiny perforations throughout its surface. Such a balloon will still retain the bone fragments and, at the same time, allow for an osmotic exchange of tissue fluids from inside the balloon to the sinus cavity and nasal vestibulum. Suitable elastomeric materials include polycarbons, from Integra Like Scienses of Plainsboro, N.J., and polytetrafluoroethylene (PTFE) made by Tef-Gen-FD of Lubbock, Tex.

Other materials which can be used for the balloon include Bovine collagen; polyethylene; resorbable Polylactic acid; resorbable lactic acid used with an elastic (resorbable or non resorbable) membrane that is sufficiently permeable to allow blood and nutrients to enter into the balloon by osmosis and contact the bone within, which promotes the growth of this bone. Also, Calcitek absorbable collagen, or Hematex by Bioplex Co. (which is an absorbable collagen hemostat) can be used.

As an alternative, the material can be elastic inert and non-resorbable as described above. In a further embodiment, the entire balloon could be non-resorbable and could remain in place to support the material bone that is within it.

Whether the balloon is resorbable or non-resorbable will have an effect on the future reestablishment of a Schneiderian membrane. For example, if the balloon remains in place the Schneiderian membrane may not grow over it unless it is made with perforations. Thus the preferred embodiment is to use a slowly resorbable balloon material for two reasons:

1. By slowly resorbing, it gives the bone that was syringed into the balloon a chance to mature so that when it finally resorbs, the bone will be solid and non-removable.

2. The Schneiderian membrane, while present, may stimulate or irritate the mucus membrane of the nose cavity to regenerate a new Schneiderian membrane by the time it resorbs.

By means of the present invention, continuation of the sub-antral bone augmentation can be accomplished immediately after a large perforation of the Schneiderian membrane. Without the present invention, the procedure would have to be aborted once the Schneiderian membrane was penetrated.

There are many cases where, due to previous chronic infections, abscesses, granulomas or from the removal of failing implants, the entire Schneiderian membrane had to be removed in order to eliminate all polypoidal and soft tissue from the sinus walls. These conditions previously contraindicated bone augmentations. However, by introducing a balloon, bone augmentations can now be carried out.

FIGS. 8 and 8A show a modified sinus balloon that can be used. Here the balloon has a tubular column 32 extending from the lip 21. At the end of the column 32 the balloon, in its deflated condition, has a number of folds 34 arranged to produce a fan-like shape, as shown in FIG. 8A, when the balloon is inflated or filled with bone chips.

The sinus balloon of FIGS. 8–8A is inserted into the antral opening as previously described and the lip 21 is glued to the walls of the bone surrounding the opening. The fan-shaped portion 34 expands as bone chips are syringed into the balloon. In many cases, it is not necessary to inflate the balloon since the folds provide an interior volume adequate to hold the necessary amount of bone fragments. The fan portion 34 can be configured as needed in terms of dimension and shape. That is, for example, the inflated fan can be relatively flat or it can be bulbous. The material for the balloon of FIGS. 8–8A can be of any of the materials previously described, but hyaluronate is preferred.

While the invention has been particularly shown and described with reference to a preferred embodiment thereof, it will be understood by those skilled in the art that various changes in form and details may be made therein without departing from the spirit and scope of the invention.

What is claimed is:

1. A method of reducing the maxillary sinus of a patient, comprising the steps of:

forming an incision through the mucoperiosteal tissue at an edentulous site to expose the surface of underlying maxillary bone of the dental arch mesial and distal to the sinus;

creating an opening completely through the exposed bone and the Schneiderian membrane at the floor of the sinus;

placing a balloon whose closed end has folds in the opening with the closed end of the balloon being within the sinus;

securing the lips of the balloon to the surface of the maxillary bone of the dental arch surrounding the opening;

inserting bone fragments through the opening in the balloon into the interior of the balloon which is within the sinus cavity to expand the closed end of the balloon into a fan shape;

closing the opening through the bone; and closing the tissue over the bone.

2. The method of claim 1 further including the step of at least partially inflating the balloon portion within the sinus cavity after the lips of the balloon are secured to the surface of the maxillary bone.

3. The method of claim 2 wherein the said step of at least partially inflating the balloon is inflated with air or helium.

4. The method of claim 2 wherein the balloon is inflated with helium.

5. The method as in claim 1 further including the steps of reopening the tissue after a sufficient period of time has elapsed for the bone inserted into the cavity to fuse and adhere to the surrounding bone of the cavity;

forming at least one opening in the dental arch in the edentulous site which extends into the inserted bone;

installing a dental implant in the at least one opening; and closing the tissue around a projecting portion of the dental implant.

6. The method of claim 5 wherein the balloon is of resorbable material and the step of reopening is delayed until the balloon has resorbed.

7. The method of claim 1 wherein the balloon is of resorbable material.

8. The method of claim 1 wherein the balloon is of non-resorbable material and at least the portion of the balloon in the sinus cavity is of a material permitting the osmotic transport of fluid into the interior of the balloon.

9. The method of claim 8 wherein said balloon portion in the sinus cavity is made of a porous elastomeric material.

10. Apparatus for closing a hole in the Schneiderian membrane of a maxillary sinus cavity formed during a dental implant operation comprising:

a balloon with a closed end and an open end with an opening surrounded by at least one lip, said balloon being of a size small enough to pass through a channel in a patient's dental maxillary arch extending to the sinus cavity in an edentulous region such that its closed end extends into the sinus cavity and the at least one lip at its open end extends out of the channel, said balloon closed end having folds and being at least partially inflatable and of sufficient strength to withstand the injection of bone fragments into it to expand said closed end into a fan shape; and means at the open end of the balloon for fastening said at least one lip to the dental arch surrounding the opening of the channel to the sinus.

11. Apparatus as claimed in claim 10 wherein the balloon is a resorbable material.

12. Apparatus as claimed in claim 10 wherein the closed end of the balloon is of non-resorbable material and the portion towards the open end of the balloon is of resorbable material.

13. Apparatus as claimed in claim 10 wherein the balloon is of non-resorbable material.

14. Apparatus as claimed in claim 10 wherein the balloon is made of a permeable material so that blood and nutrients can pass into its interior by osmosis.

15. Apparatus as claimed in claim 10 wherein the material of at least a part of the balloon is selected from the group consisting of polylactate, bovine collagen, polyethylene, resorbable Polylactic acid, resorbable lactic acid with an elastic (resorbable or non resorbable) membrane, hyaluronate, Calcitek absorbable collagen, and Hematex absorbable collagen hemostat, and polytetrafluorethylene (PTFE) non-absorbable guided tissue membrane.

* * * * *